////United States Patent [19]

Wheeler et al.

[11] 4,263,446
[45] Apr. 21, 1981

[54] PROCESS FOR MAKING 3-(3,5-DIALKYL-4-HYDROXYPHENYL)PROPIONATE ESTERS OF HYDROXYALKYLOXAMIDES

[75] Inventors: Edward L. Wheeler, Watertown; Elmar H. Jancis, Naugatuck, both of Conn.

[73] Assignee: Uniroyal, Inc., New York, N.Y.

[21] Appl. No.: 43,788

[22] Filed: May 30, 1979

[51] Int. Cl.$^3$ .......................................... C07C 69/612
[52] U.S. Cl. ...................................................... 560/75
[58] Field of Search ........................................ 560/75

[56] References Cited

U.S. PATENT DOCUMENTS

| | | | |
|---|---|---|---|
| 4,085,132 | 4/1978 | Park et al. | 560/75 |
| 4,145,556 | 3/1979 | Hirsch et al. | 560/193 |
| 4,153,597 | 5/1979 | Wheeler et al. | 560/75 |

OTHER PUBLICATIONS

M & T Chemicals Inc., Rahway, New Jersey, product description sheet Nos. 342 and 346.
Nagai et al., "Chem. Absts.", 87, 53825(a), 1977.
Hamada et al., "Chem. Absts.", 85, 78684(a), 1976.
Koseki et al., "Chem. Absts.", 87, 118421(n) 1977.

*Primary Examiner*—Natalie Trousof
*Assistant Examiner*—G. T. Breitenstein
*Attorney, Agent, or Firm*—Thomas A. Beck

[57] ABSTRACT

An improved method for making 3-(3,5-dialkyl-4-hydroxyphenyl)propionates of hydroxyalkyloxamides involved heating the hydroxyalkyloxamide with a lower alkyl ester of 3-(3,5-dialkyl-4-hydroxyphenyl)-propionic acid in the presence of an alkanestannoic acid at a temperature of 150° to 230° C., the lower boiling alcohol being removed by distillation.

5 Claims, No Drawings

PROCESS FOR MAKING 3-(3,5-DIALKYL-4-HYDROXYPHENYL)PROPIONATE ESTERS OF HYDROXYALKYLOXAMIDES

BACKGROUND OF THE INVENTION

Hydroxyalkyloxamide esters of 3-(3,5-dialkyl-4-hydroxyphenyl)propionic acid are excellent stabilizers and antioxidants for a variety of organic materials. They are described in U.S. Pat. No. 4,145,556 and in the inventor's copending applications, Ser. No. 043,790, entitled "N,N$^1$-Bis-2-3-(3,5-di-tert.-butyl-4-hydroxyphenyl)propionyloxy ethyl oxamide", Ser. No. 043,914, now abandoned, entitled "Phenolic Oxamide Antioxidants", and Ser. No. 043,761, entitled "Polyfunctional Phenolic Oxamide Antioxidants", assigned to Uniroyal, Inc., filed on even date herewith, the disclosures of which are hereby incorporated by reference: These esters can be made by the usual esterification or transesterification methods. The use of tin type transesterification catalysts is of particular value in making esters of 3-(3,5-di-alkyl-4-hydroxyplenyl)propionic acid. Strong acid catalysts tend to remove some of the tertiary alkyl groups from the phenolic ring during the transesterification. Strong bases tend to split the propionate into di-alkyl phenol and an acrylate. Tin catalysts are not known to promote either of these side reactions. They also have the advantage of being useful at very low concentrations (0.1–0.25%). A variety of tin transesterification catalysts are commercially available. The literature teaches that temperatures around 220° C. are needed for a satisfactory rate. This presents a drawback in their use as many esters can decompose at that temperature.

It has surprisingly been found that in the case of transesterification with lower alkyl 3-(3,5-di-alkyl-4-hydroxyphenyl)propionates, using certain tin transesterification catalysts, the transesterification begins to take place at temperatures as low as 150° C.

SUMMARY OF THE INVENTION

The present invention relates to a process for making esters of the formula [—CONHA$+$OCOR)$_n$]$_2$, wherein R is a 2(3,5-di-Z-4-hydroxyphenyl)ethyl radical, A is a $C_2$ to $C_{12}$ linear or branched hydrocarbyl radical of the valence n+1, n is an integer 1 to 3 and Z is a linear or branched $C_1$ to $C_9$ alkyl comprising heating a $C_1$ to $C_4$ linear or branched alkyl ester of 3-(3,5-di-W-4-hydroxyphenyl)propionic acid wherein Z is as defined above, with an alcohol of the formula [—CONHA$+$OH)$_n$]$_2$, wherein A and n are as defined above, in the presence of an linear or branched alkanestannonic acid at a temperature of from 150° to 230° C., the lower boiling alcohol being removed by distillation.

DESCRIPTION OF THE PREFERRED EMBODIMENTS

The preferred catalyst is butane stannonic acid. It was surprising that butane stannonic acid is a more active catalyst than either dibutyltin oxide or stannous oxalate, as the literature showed the latter two catalysts to be more active than butane stannonic acid in the esterification of octyl alcohol with phthalic anhydride.

The preferred temperature for the transesterification varies somewhat with the alcohol being esterified, but generally lies in the range 165° to 195° C. Discoloration of the product can at times be observed at temperatures above 200° C. The transesterification can be run advantageously without a solvent. The amount of lower alkanol distilled off provides a good measure of the completeness of the reaction. The reaction goes at low catalyst concentrations (0.1%), but somewhat higher concentrations (0.2–0.5%) are often preferred. Bases should preferably be excluded from this reaction as bases can deactivate the catalyst.

The 3-(3,5-di-tert-butyl-4-hydroxyphenyl)propionate used as a starting material can be made from a lower alkyl acrylate and 2,6-dialkylphenol according to procedures described in U.S. Pat. No. 3,247,240. The methyl ester, claimed in U.S. Pat. No. 3,364,250, is particularly active in this process. The process consists of reacting 2,6-di-tert-butylphenol with a lower alkyl acrylate in the presence of a basic catalyst such as potassium tert-butoxide. The hydroxyalkyl oxamides useful as starting materials in this invention can be readily made by reacting amine alcohols with dialkyl oxalates, oxalic acid or oxalyl halide. An acid acceptor is used to advantage if an oxalyl halide is the reagent used.

Convenient aminoalcohols used in the preparation of the compounds of the present invention include: ethanolamine, 2-aminopropanol, 2-amino-2-methyl-1-propanol, 3-amino-2-methyl-1-propanol, 2-amino-1-butanol, 2-amino-2-methyl-1,3-propanediol, 2-amino-2-ethyl-1,3-propanediol, tris(hydroxymethyl)aminomethane, 1-amino-1-cyclopentanemethanol, 1-aminomethyl-1-cyclohexanemethanol, 6-amino-1-hexanol, 2-amino-3-methyl-1-butanol, 5-amino-1-pentanol, 3-amino-1,2-propanediol, 3-amino-1-propanol, 2-aminocyclohexanol, 4-amino-cyclohexanol, 3-amino-2-butanol, 1-amino-2-dodecanol, 2,2-di-methyl-3-amino-1-propanol, 2-aminomethyl-2-methyl-1,3-propanediol, 2,2,2,-tris-(hydroxymethyl) aminoethane. Many other amino alcohols are readily made by known methods from available starting materials.

To drive the reaction to completion, the lower boiling alcohol has to be removed by distillation. To facilitate the distillation, a vacuum can be applied to the reaction vessel or an inert gas can be bubbled through the reaction. The use of an excess of the ester is generally recommended to drive the reaction to completion. The excess lower alkyl 2-(3,5-di-alkyl-4-hydrolyphenyl)propionate is generally more soluble in hexane than the product, and can be washed out from the product with hexane.

The following non-limiting examples further illustrate the use of this invention.

EXAMPLE 1

This example shows the superiority of butane stannonic acid over dibutyltin oxide and stannous oxalate in esterifying N,N'-bis(2-hydroxyethyl)oxamide.

A mixture of 161 g (0.53 mole) of ethyl 2-(3,5-di-tert-butyl-4- hydroxyphenyl)propionate, 44 g (0.25 mole) N,N'-bis(2-hydroxyethyl) oxamide, 1 g butane stannonic acid was heated to 175° C., nitrogen was passed through the reaction mixture for 6 hours. At the end of the first hour, 16 g (70%) of ethanol was collected in the dry ice trap. After six hours 21 g (91%) of ethanol was collected.

The hot melt was poured into super VM & P naptha solvent. On cooling, 163 g (93.7%) of N,N'-oxamido bis [2-ethyl-2-(3,5-di-tert-butyl-4-hydroxyphenyl)propionate] was obtained.

When 1 g of stannous oxalate was substituted in the above reaction, only 2 g (9%) of ethanol was collected in the first hour, and only 5.1 g (22%) of ethanol was collected at the end of six hours.

When 1 g of dibutyltin oxide was substituted in the above reaction, only 6.5 g (28.1%) of ethanol was collected in the first hour, and only 18 g (78%) of ethanol was collected at the end of six hours.

We claim:

1. A process for making esters of the formula $[-CONHA-(OCOR)_n]_2$, wherein R is a 2-(3,5-di-Z-4-hydroxyphenyl)ethyl radical, A is a $C_2$ to $C_{12}$ linear or branched hydrocarbyl radical of the valence $n+1$, n is an integer 1 to 3 and Z is a linear or branched $C_1$ to $C_9$ linear or branched alkyl, comprising heating a $C_1$ to $C_4$ alkyl ester of 3-(3,5-di-Z-4-hydroxyphenyl)propionic acid wherein Z is as defined above, with an alcohol of the formula $[-CONHA-(OH)_n]_2$, wherein A and n are as defined above, in the presence of an linear or branched alkanestannonic acid at a temperature of from 150°–230° C., the lower boiling alcohol being removed by distillation.

2. A process according to claim 1, wherein the 2-(3,5-di-alkyl-4-hydroxyphenyl)ethyl radical is the 2-(3,5-di-tert-butyl-4-hydroxyphenyl)ethyl radical.

3. A process according to claim 2, wherein n is 1 and A is ethylene.

4. A process according to any one of claims 1 to 3, wherein the catalyst is butanestannonic acid.

5. A process according to claim 1, wherein said temperature is from 165° to 195° C.

* * * * *